United States Patent [19]

Klohs et al.

[11] Patent Number: 5,160,727
[45] Date of Patent: Nov. 3, 1992

[54] TUMOR CELL SENSITIZATION METHOD USING QUINAZOLINEDIONE DERIVATIVES

[75] Inventors: Wayne Klohs, Ann Arbor, Mich.; Avner Ramu, Jerusalem, Israel

[73] Assignees: Warner-Lambert Company, Morris Plains, N.J.; Hadasit Medical Research Services and Development, Jerusalem, Israel

[21] Appl. No.: 497,049

[22] Filed: Mar. 21, 1990

Related U.S. Application Data

[63] Continuation-in-part of Ser. No. 479,320, Feb. 13, 1990, abandoned.

[51] Int. Cl.$^5$ .................. A61K 49/00; A61K 31/70; A61K 31/525; A61K 31/44
[52] U.S. Cl. ........................ 424/10; 514/34; 514/259; 514/283; 514/258; 514/253
[58] Field of Search ................ 424/10; 544/285; 514/258, 259, 260, 283

[56] References Cited

U.S. PATENT DOCUMENTS

| | | | |
|---|---|---|---|
| 3,819,630 | 6/1974 | Parcell | 544/285 |
| 4,564,616 | 1/1986 | Jones et al. | 514/260 |
| 4,578,465 | 3/1986 | Nagano et al. | 544/285 |
| 4,705,787 | 11/1987 | Ueda et al. | 514/259 |
| 4,981,856 | 1/1991 | Hughes | 514/259 |

OTHER PUBLICATIONS

A. Ramu, "Structure–Activity Relationship of Compounds that Restore Sensitivity to Doxorubicin in Drug-Resistant P388 Cells", *Resistance to Antineoplastic Drugs,* Ch. 5, pp. 63–80 (1987).

*Primary Examiner*—Jerome D. Goldberg
*Assistant Examiner*—T. J. Criares
*Attorney, Agent, or Firm*—Ruth H. Newtson

[57] ABSTRACT

A method for sensitizing cancer cells which have become resistant to treatment with one or more anticancer agents which comprises treating said cells with a quinazolinedione compound.

2 Claims, No Drawings

TUMOR CELL SENSITIZATION METHOD USING QUINAZOLINEDIONE DERIVATIVES

This is a continuation-in-part of U.S. application Ser. No. 479,320 filed Feb. 13, 1990, now abandoned.

BACKGROUND OF THE INVENTION

Resistance to multiple chemotherapeutic agents is a common clinical problem in the treatment of cancer. Such drug resistance may occur in primary therapy or be acquired during treatment. The problem is further exacerbated by the observation that these tumors are often cross-resistant to other drugs even though these drugs were not used in the initial treatment. Experimentally, this phenomenon is known as multidrug resistance (MDR) and appears to be use in part to an enhanced drug efflux mechanism which results in a reduced intracellular level of drug, although it is clear that multiple mechanisms can contribute to the MDR phenotype.

The hallmark of MDR is the overexpression of a membrane glycoprotein, termed P-glycoprotein (P-gp), which is thought to be responsible for the energy-dependent nonspecific exodus of drugs from MDR cells. Recent evidence from the transfection of the gene encoding for P-gp into drug-sensitive cells and the subsequent expression of the MDR phenotype in these cells confirms the importance of P-gp in MDR.

A broad range of agents that have been shown to modulate drug activity in MDR tumor cells. These include calcium channel blockers such as verapamil, steroids, and steroid antagonists (progesterone and tamoxifen), calmodulin antagonists (trifluoperazine), immunosuppressants (cyclosporin A), and cardiac agents (quinidine and aminodarone). These agents, however, have two major problems: (1) adequate blood levels for chemosensitization of MDR tumors cannot be achieved without considerable toxicity, and (2) most of these agents do not fully restore chemosensitivity of MDR tumors to anticancer drugs.

We have discovered a class of agents that addresses both of these problems. We have found a class of quinazolinedione compounds that are able to fully sensitize MDR cells to anticancer agents, and in limited clinical trials as antipsychotic drugs adequate plasma levels of representative examples of these drugs for chemosensitization of MDR tumors were achieved.

INFORMATION DISCLOSURE

Quinazolinedione compounds of the type employed in this invention are disclosed in U.S. Pat. No. 3,819,630 as having cerebral depressant activity and as suppressing conditioned avoidance behavior.

A review of the structure activity relationship of a large number of compounds reported to circumvent multiple drug resistance of cells to doxorubicin is reported by Avner Ramu in *Resistance to Antineoplastic Drugs* ed., D. Kessel, CRC Press, Inc., Boca Raton, Fla., 1989, Chapter 5, pp. 63–80 entitled "Structure-Activity Relationship of Compounds That Restore Sensitivity Doxorubicin In Drug-Resistance P388 Cells."

SUMMARY OF THE INVENTION

Compounds of the following general formula are useful in sensitizing multiple drug resistance (MDR) cells to anticancer agents:

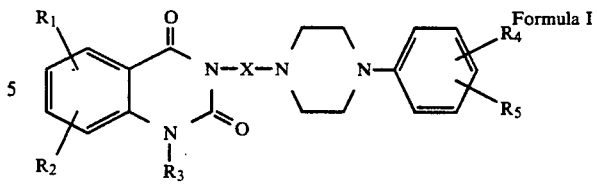

wherein
  X is an alkylene chain having from three to seven carbon atoms;
  each of $R_1$ and $R_2$ is hydrogen, chlorine, fluorine, bromine, or lower alkoxy having from one to four carbon atoms and which is straight or branched;
  $R_3$ is hydrogen or a straight or branched lower alkyl of from one to three carbon atoms;
  each of $R_4$ and $R_5$ is hydrogen, chlorine, fluorine, bromine, or lower alkylthio having from one to four carbon atoms and which is straight or branched with proviso that one of $R_4$ and $R_5$ is other than hydrogen;
or a pharmaceutically acceptable acid-addition salt thereof.

The compounds of general Formula I are useful in treating patients having cancer and who have developed a resistance to one or more chemotherapeutic agents. By administering to such patients a compound of Formula I, drug resistant cells of the patient are sensitized or modified rendering said cells sensitive to the chemotherapeutic agent(s) once again, thereby permitting treatment of the patient with said agent(s) to resume or continue.

The present invention provides a method for reversing multiple drug resistance to anticancer agents in a cancer cell which comprises treating said cell with an amount of a compound of the above Formula I capable of reversing said resistance.

The present invention also provides a method for rendering multiple drug-resistant cancer cells sensitive to anticancer agents which comprises treating said cells with an effective amount of a compound of the above Formula I.

The present invention further provides a method of treating a patient having cancer cells which are resistance to multiple drugs which comprises administering to said patient an anticancer agent and an amount of a compound of the above Formula I which is capable of rendering the resistance cells sensitive to anticancer agents.

The present invention also provides a method for increasing drug accumulation and cytotoxicity in multiple drug-resistant cancer cells which comprises treating said cells with an amount of compound of the above Formula I which is capable of increasing said drug accumulation.

DETAILED DESCRIPTION OF INVENTION

In general Formula I, X represents an alkylene moiety having from three to seven carbon atoms and may also be represented by the group $-(CH_2)_n-$ wherein n is an integer of from three to seven.

Illustrative lower alkoxy groups having from one to four carbon atoms and being straight or branched which $R_1$ and $R_2$ may represent are methoxy, ethoxy, n-propoxy, isopropoxy, n-butoxy, tert-butoxy, and isobutoxy.

The group $R_3$ represents hydrogen or a lower alkyl group having from one to three carbon atoms being methyl, ethyl or n-propyl, or isopropyl.

The alkylthio group which $R_4$ and $R_5$ may represent may be depicted as the group alkyl $C_{1-4}$—S— wherein the alkyl group is straight or branched, for example, methylthio, ethylthio, n-propylthio, isopropylthio, n-butylthio, isobutylthio and tertbutylthio.

The compounds of general Formula I are prepared as described in U.S. Pat. No. 3,819,630 the relevant portions of which are incorporated herein by reference thereto and in particular column 1, lines 53 to 72, and all of columns 2 through 6. The procedure for obtaining the compounds of Formula I are depicted in Charts I and II which generally is the same as the description found in U.S. Pat. No. 3,819,630. In Chart I n is three to seven, $R_6$ is alkyl $C_{1-3}$, and all other symbolic representations are the same as in Formula I. In Chart II, all symbolic representations are the same as in Formula I and compound (5) can be treated as shown in Chart I to obtain compounds of Formula I.

The compounds of Formula I including acid-addition salts thereof are useful in sensitizing or modifying cancer cells in a patient which have become resistant to one or more anticancer agents. The Formula I compounds are capable of sensitizing virtually any cancer cell which has become multidrug resistant (MDR). There is a large number of anticancer agents which are known to be involved in MDR or result under clinical therapeutic conditions in cancer cells becoming resistant to treatment. Such anticancer agents include the vinca alkaloids, such as, vinblastine and vincristine; anthyacyclines, such as, doxorubicin and daunorubicin; lipophilic antifolates, such as, trimetrexate and piritrexim; epipodophyllotoxins, such as, etoposide; synthetic analogs such as the anthrapyrazoles described in U.S. Pat. No. 4,556,654 specifically for example 7,10-dihydroxy-2-[2-[(2-hydroxyethyl)amino]ethyl]-5-[[2-(methylamino)ethyl]amino]anthra[1,9-cd]pyrazol-6(2H)-one dihydrochloride (CI-937) or the benzothiopyranoindazoles described in U.S. Pat. No. 4,604,390 specifically 5-[(2-aminoethyl)amino]-2-[2-(diethylamino)ethyl]-2H-[1]benzothiopyrano[4,3,2-cd]indazol-8-ol trihydrochloride (CI-958), and taxol.

In practicing the present invention the compounds of general Formula I will find use as soon as the drug resistant cancer patient is identified, i.e., the occurrence of the identification of a patient who is not responding to therapy due to the fact that the cancer cells of that patient have become resistant to the anticancer agent or agents with which the patient has been treated. Typically, such patient is treated initially with high doses of the Formula I compound to obtain sufficient blood levels to sensitize the cancer cells. The high dose will vary from compound to compound but typically would be 1000 mg to 2000 mg per day for 1 or 2 days, preferably 1 day. Once adequate blood levels of the sensitizing compound are achieved the dosage amount is reduced to a level adequate to maintain blood levels of compound and anticancer therapy is resumed. Typically the "maintenance" dose of a compound of Formula I would be from 200 mg to 400 mg of compound given three times per day. Anticancer therapy would be continued in the same manner as prior to the patient having been diagnosed as drug resistant except that the anticancer agent(s) is co-administered with maintenance dose of sensitizing compound.

In practicing the present invention the compounds of Formula I can be administered orally or parenterally, particularly intravenously or subcutaneously. Oral administration is preferred.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about five to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage from suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methylcellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

Preferred compounds of Formula I for use in practicing the present invention are those wherein X is butylene, i.e., —$(CH_2)_4$—, $R_4$ is hydrogen, and $R_5$ is a propylthio group. Compounds wherein $R_5$ is propylthio in the 2-position are most preferred.

Illustrative examples of compounds of Formula I include the following:

| Example No. | Name |
| --- | --- |
| 1 | 3-[4-[4-[2-(propylthio)-phenyl]-1-piperazinyl]-butyl-2,4-(1H,3H)-quina- |

| Example No. | Name |
|---|---|
| | zolinedione (tioperidone) monohydrochloride |
| 2 | 3-[3-[4-[2-(propylthio)-phenyl]-1-piperazinyl]-propyl]-2,4-(1H,3H)-quinazolinedione monohydrochloride |
| 3 | 6-chloro-3-[4-[4-[2-(propylthio)phenyl]-1-piperazinyl]-butyl]-2,4-(1H,3H)quinazolinedione monohydrochloride |
| 4 | 3-[4-[4-(2,3-dichlorophenyl)-1-piperazinyl]-butyl]-2,4-(1H,3H)-quinazolinedione monohydrochloride |
| 5 | 3-[4-[4-[2-(ethylthio)-phenyl]-1-piperazinyl]-butyl]-2,4-(1H,3H)-quinazolinedione monohydrochloride |
| 6 | 3-[4-[4-[2-[(1-methylethyl)thio]phenyl]-1-piperazinyl]-butyl]-2,4-(1H,3H)-quinazolinedione monohydrochloride |
| 7 | 3-[4-[4-[2-methylthio)-phenyl]-1-piperazinyl]-butyl]-2,4(1H,3H)quinazolinedione monohydrochloride |
| 8 | 3-[4-[4-[2-(butylthio)-phenyl]-1-piperazinyl]butyl]-2,4-(1H,3H)-quinazolinedione monohydrochloride |
| 9 | 7-chloro-3-[4-[4-[2-(propylthio)phenyl]-1-piperazinyl]-butyl]2,4(1H,3H)-quinazolinedione monohydrochloride |
| 10 | 6-methyl-3-[4-[4[2(propylthio)phenyl]-1-piperazinyl]-butyl]-2,4(1H,3H)-quinazolinedione monohydrochloride |
| 11 | 3-[6-[4-[2-(propylthio)-phenyl]-1-piperazinyl]-hexyl]-2,4-(1H,3H)quinazolinedione monohydrochloride, ½ hydrate |
| 12 | 1-methyl-3-[4-[4-[2-(propylthio)phenyl]-1-piperazinyl]-butyl]-2,4-(1H,3H)quinazolinedione |
| 13 | 6,7-dimethoxy-3-[4-[4-[2-(propylthio)phenyl]-1-piperazinyl]butyl]-2,4-(1H,3H)-quinazolinedione |
| 14 | 6,7-dimethoxy-3-[5-[4-[2-(propylthio)phenyl]-1-piperazinyl]pentyl]-2,4(1H,3H)-quinazolinedione |
| 15 | 6,7-dimethoxy-1-methyl-3-[4-[4-[2-(propylthio)-phenyl]-1-piperazinyl]-butyl]-2,4(1H,3H)-quinazolinedione |
| 16 | 6,7-dimethoxy-1-methyl-3-[5-[4-[2-(propylthio)-phenyl]-1-piperazinyl]-pentyl]-2,4(1H,3H)-quinazolinedione |
| 17 | 8-methoxy-3-[4-[4-[2-(propylthio)phenyl]-1-piperazinyl]butyl]-2,4-(1H,3H)quinazolinedione |
| 18 | 8-methoxy-1-methyl-3-[4-[4-[2-(propylthio)phenyl]-1-piperazinyl]butyl]-2,4-(1H,3H)quinazolinedione monohydrochloride |
| 19 | 3-[5-[4-[2-(propylthio)-phenyl]-1-piperazinyl]-pentyl]-2,4-(1H,3H)-quinazolinedione |

| Example No. | Name |
|---|---|
| | zolinedione |

In comparative studies of potential chemosensitizers for MDR, including verapamil, amiodarone, and cyclosporin A, which are three agents currently in clinical trials as chemosensitizers, we found that tioperidone (Example 1) was superior to all of the other agents in potentiating the activity of adriamycin in P388R cells which are murine leukemia cells having resistance to a variety of drugs. As with cyclosporin A and verapamil, tioperiodone had little effect on adriamycin activity in the drug-sensitive parent P388S cells. Tioperidone fully sensitized P388R cells to vincristine, trimetrexate, and the anthrapyrazole, CI-937. Tioperidone chemosensitizes MDR P388 cells by increasing the intracellular drug levels. Unlike amiodarone, whose chemosensitizing activity is diminished by binding to serum proteins, the activity of tioperidone in MDR cells does not appear to be altered by serum proteins. In performing the studies P388 that were sensitive to adriamycin (P388S) and P388 cells that were resistant to adriamycin (P388/ADR) were exposed to various concentrations of anticancer drug either alone or together with 5 µg/mL of modifier or sensitizer for 72 hours. The results are set forth in the following Table I wherein the effect of the anticancer drug alone or in combination with the modifier is expressed as the $ID_{50}$ which is the concentration that inhibits 72-hour cell growth by 50%.

In Table I, TIOP means tioperidone, VER means verapamil, and CsA means cyclosporin A.

TABLE

| Drug | Modifier (5 µg/mL) | $ID_{50}$ (nM)[a] | |
|---|---|---|---|
| | | P388S | P388/ADR |
| Adriamycin | None | 156 | 7819 |
| | TIOP | 152 | 174 |
| | VER | 152 | 710 |
| | CsA | 147 | 195 |
| 7,10-Dihydroxy-2-[2-[(2-hydroxyethyl)amino]ethyl]-5-[[2-(methylamino)-ethyl]amino]anthra-[1,9-cd]pyrazol-6(2H)-one dihydrochloride (CI-937) | None | 145 | 5733 |
| | TIOP | 145 | 132 |
| | VER | 147 | 524 |
| | CsA | 135 | 151 |
| Daunomycin | None | 98 | 2773 |
| | TIOP | 96 | 103 |
| | VER | 93 | 329 |
| | CsA | 95 | 108 |
| Vincristine | None | 21 | 554 |
| | TIOP | 20 | 22 |
| | VER | 21 | 30 |
| | CsA | 21 | 27 |
| Trimetrexate | None | 12 | 270 |
| | TIOP | 12 | 14 |
| | VER | 12 | 29 |
| | CsA | 11 | 12 |
| Etoposide | None | 24.1 | 5100 |
| | TIOP | 21.2 | 433 |
| | VER | 20.1 | 872 |
| | CsA | 19.8 | 252 |

[a]Results are the mean of two experiments, each performed in triplicate.

The results of additional studies demonstrating the ability of compounds of Formula I to potentiate the activity of adriamycin in P388 resistant cells are set forth in the following Table II.

TABLE II

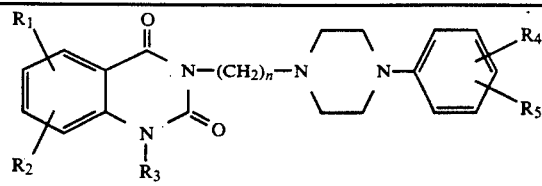

Test Compound

| Example No. | $R_1$ | $R_2$ | $R_3$ | n | $R_4$ | $R_5$ | % of Control Cell Growth at 5 μM | 10 μM | Degree of ADR[a] Potentiation in P388R 5 μM | 10 μM |
|---|---|---|---|---|---|---|---|---|---|---|
| 1 | H | H | H | 4 | H | 2-S-n-$C_3H_7$ | 100 | 98 | 20.8 | 44.7 |
| 2 | H | H | H | 3 | H | 2-S-n-$C_3H_7$ | 89 | 87 | 13.1 | 22.0 |
| 3 | H | 6-Cl | H | 4 | H | 2-S-n-$C_3H_7$ | 100 | 88 | 19.6 | 44.7 |
| 4 | H | H | H | 4 | 2-Cl | 3-Cl | 76 | 76 | 21.8 | 31.7 |
| 5 | H | H | H | 4 | H | 2-S—$C_2H_5$ | 79 | 78 | 19.6 | 46.6 |
| 6 | H | H | H | 4 | H | 2-S-i-$C_3H_7$ | 91 | 59 | 24.2 | 52.2 |
| 7 | H | H | H | 4 | H | 2-S—$CH_3$ | 95 | 72 | 25.2 | 48.4 |
| 8 | H | H | H | 4 | H | 2-S-n-$C_4H_9$ | 88 | 86 | 25.0 | 48.4 |
| 9 | H | 7-Cl | H | 4 | H | 2-S-n-$C_3H_7$ | 100 | 85 | 22.2 | 35.4 |
| 10 | H | 6-$CH_3$ | H | 4 | H | 2-S-n-$C_3H_7$ | 92 | 85 | 21.0 | 48.4 |
| 11 | H | H | H | 6 | H | 2-S-n-$C_3H_7$ | 99 | 66 | 73.8 | 52.2 |
| 12 | H | H | $CH_3$ | 4 | H | 2-S-n-$C_3H_7$ | 100 | 87 | 17.9 | 39.1 |
| 13 | 6-$OCH_3$ | 7-$OCH_3$ | H | 4 | H | 2-S-n-$C_3H_7$ | 100 | 10.4 | 93.0 | 52.2 |
| 14 | 6-$OCH_3$ | 7-$OCH_3$ | H | 5 | H | 2-S-n-$C_3H_7$ | 53 | 1.2 | 65.0 | — |
| 15 | 6-$OCH_3$ | 7-$OCH_3$ | $CH_3$ | 4 | H | 2-S-n-$C_3H_7$ | 46 | 2.6 | 21.2 | — |
| 16 | 6-$OCH_3$ | 7-$OCH_3$ | $CH_3$ | 5 | H | 2-S-n-$C_3H_7$ | 33 | 4.2 | 44.5 | — |
| 17 | H | 8-$OCH_3$ | H | 4 | H | 2-S-n-$C_3H_7$ | 83 | 39 | 3.4 | 67.2 |
| 18 | H | 8-$OCH_3$ | $CH_3$ | 4 | H | 2-S-n-$C_3H_7$ | 100 | 87 | 21.1 | 24.6 |
| 19 | H | H | H | 5 | H | 2-S-n-$C_3H_7$ | 100 | 68 | 36.7 | 66.9 |

[a] Degree of potentiation = $\dfrac{ID_{50} \text{ of P388R } - \text{ test compound}}{ID_{50} \text{ of P388R } + \text{ test compound}}$ The P388 murine leukemia cells used in obtaining the data set forth in Table I and Table II were obtained from Southern Research Institute (Birmingham, Ala.) and were cultured from ascites fluids of tumor-bearing DMA/2 mice and maintained in Fischer's medium supplemented with 10% horse serum, 10 μM 2-mercaptoethanol, and gentamycin (50 μg/mL). Cells were counted with a Model ZF Coulter Counter (Coulter Electronics, Inc., Hialeah, Fla.). Viability was determined by trypan blue exclusion. The general methodology is described by W. D. Klohs, et al, Cancer Research 46, 4352–4356 (September 1986) and W. D. Klohs, et al, J. Nat'l. Cancer Inst. 75, 353–359 (1985).

The use of the compounds of Formula I in practicing the present invention is further illustrated by the following example of treatment of a patient.

A patient having MDR leukemia and identified as not responding to anticancer treatment with drugs that are known to be included in the MDR group is subjected to the following dosage regimen of tioperidone and adriamycin over a three-day period.

| Treatment Day | Adriamycin | Tioperiodone |
|---|---|---|
| 1 | — | 1500 mg |
| 2 | 60 mg/m² | 1000 mg |
| 3 | 60 mg/m² | 1000 mg |
| 4 | 60 mg/m² | 1000 mg |
| 5 | 60 mg/m² | 1000 mg |
| 7 | — | 1000 mg |

Following treatment, results are measured by observing bone marrow and/or blood levels of leukemia cells.

CHART I

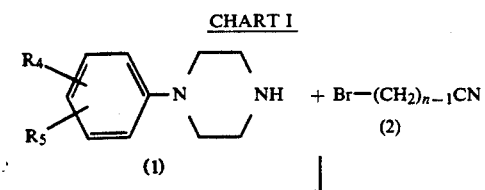

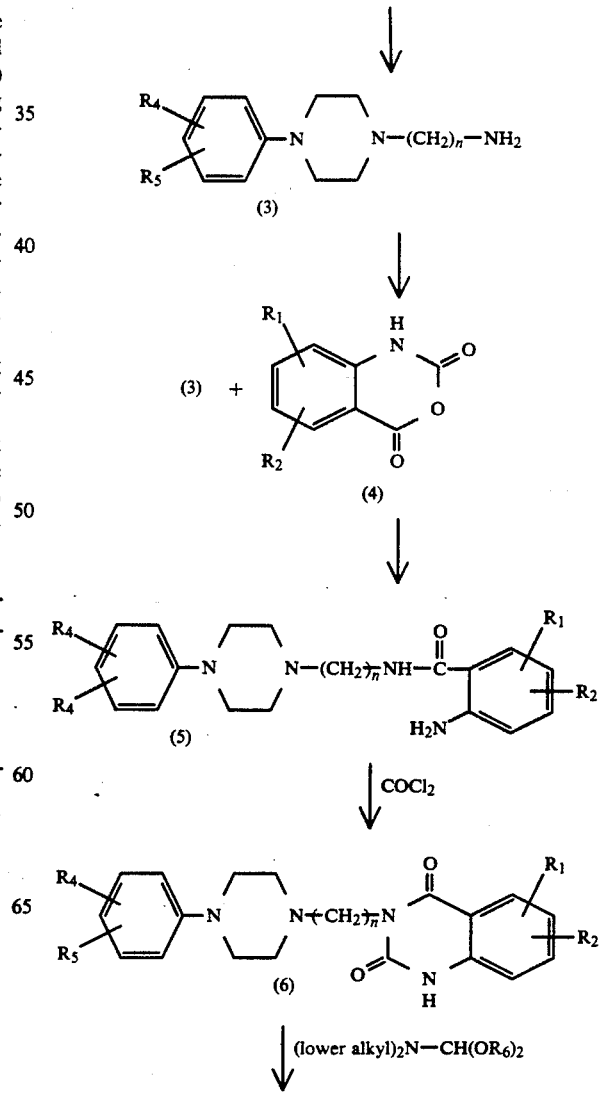

CHART I-continued

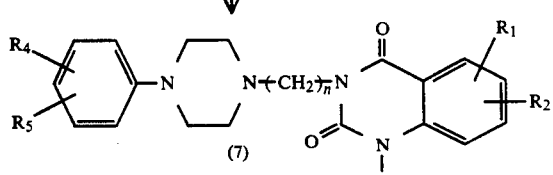

CHART II

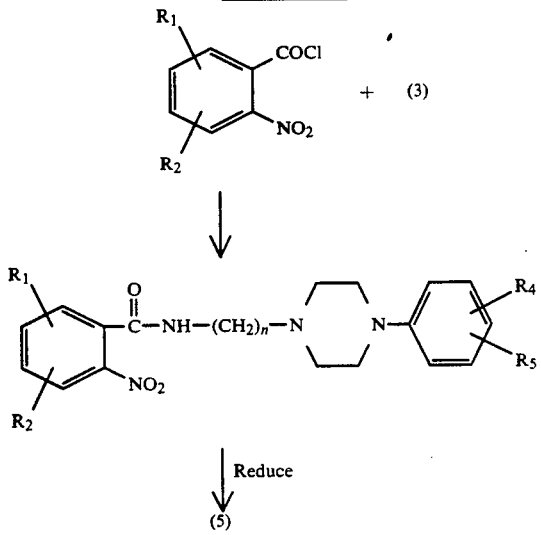

We claim:

1. A method of treating a patient having cancer cells which are resistance to multiple drugs which comprises administering to said patient an anticancer agent selected from the group consisting of vinblastine, vincristine, doxorubicin, daunorubicin, trimetrexate, piritrexim, etoposide, 7,10-dihydroxy-2-[2-[(2-hydroxyethyl)amino]ethyl]-5-[[2-(methylamino)ethyl]amino]anthra[1,9-cd]pyrazol-6-(2H)-one dihydrochloride, 5-[(2-aminoethyl)amino]-2-[2-(diethylamino)ethyl]-2H-[1]benzothiopyrano[4,3,2-cd]indazol-8-ol trihydrochloride, and taxol and an amount of a compound of the following formula which is capable of rendering the resistant cells sensitive to anticancer agents:

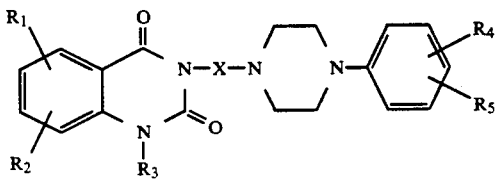

wherein X is an alkylene chain having from three to seven carbon atoms; each of $R_1$ and $R_2$ is hydrogen, chlorine, fluorine, bromine, or lower alkoxy having from one to four carbon atoms and which is straight or branched; $R_3$ is hydrogen or a straight or branched lower alkyl of from one to three carbon atoms; each of $R_4$ and $R_5$ is hydrogen, chlorine, fluorine, bromine, or lower alkylthio having from one to four carbon atoms and which is straight or branched with the proviso that one of $R_4$ and $R_5$ is other than hydrogen; or a pharmaceutically acceptable acid-addition salt thereof.

2. The method of claim 1 wherein the compound is tioperidone.

* * * * *

UNITED STATES PATENT AND TRADEMARK OFFICE
CERTIFICATE OF CORRECTION

PATENT NO.   : 5,160,727
DATED        : November 3, 1992
INVENTOR(S)  : Wayne Klohs and Avner Ramu It is certified that error appears in the above-indentified patent and that said Letters Patent is hereby corrected as shown below:

Column 9, line 36, delete "resistance" and insert --resistant--.

Signed and Sealed this

Twelfth Day of October, 1993

Attest:

Attesting Officer

BRUCE LEHMAN

Commissioner of Patents and Trademarks